United States Patent
Miele et al.

(10) Patent No.: US 12,404,282 B2
(45) Date of Patent: Sep. 2, 2025

(54) PROCESS FOR THE PURIFICATION OF INDOLE CARBAZOLE ALKALOIDS

(71) Applicant: INDENA S.P.A., Milan (IT)

(72) Inventors: Katia Miele, Milan (IT); Luca Domenighini, Milan (IT); Daniele Ciceri, Milan (IT)

(73) Assignee: INDENA S.P.A., Milan (IT)

( * ) Notice: Subject to any disclaimer, the term of this patent is extended or adjusted under 35 U.S.C. 154(b) by 403 days.

(21) Appl. No.: 17/905,327

(22) PCT Filed: Mar. 1, 2021

(86) PCT No.: PCT/IB2021/051683
§ 371 (c)(1),
(2) Date: Aug. 30, 2022

(87) PCT Pub. No.: WO2021/176328
PCT Pub. Date: Sep. 10, 2021

(65) Prior Publication Data
US 2023/0128149 A1    Apr. 27, 2023

(30) Foreign Application Priority Data
Mar. 2, 2020 (IT) .......................... 102020000004291

(51) Int. Cl.
*C07D 498/22* (2006.01)
(52) U.S. Cl.
CPC .................. *C07D 498/22* (2013.01)
(58) Field of Classification Search
CPC ..................................... C07D 498/22
See application file for complete search history.

(56) References Cited

U.S. PATENT DOCUMENTS

2005/0159404 A1    7/2005    Si et al.

FOREIGN PATENT DOCUMENTS

CA    1337763 C    12/1995

OTHER PUBLICATIONS

Satoshi O et al., "A new alkaloid AM-2282 of Streptomyces origin taxonomy, fermentation, isolation and preliminary characterization", The Journal of Antibiotics, vol. 30, No. 4, Jan. 1, 1977, pp. 275-282.
Search Report and Written Opinion of PCT/IB2021/051683 issued May 31, 2021.
Wermuth C. et al. , "Chapter II: Selected procedures for the preparation of pharmaceutically acceptable salts", Jan. 1, 2008 Hnadbook or Pharmacetucal Salts, Helvetica Chimica Acta, pp. 219-263.

*Primary Examiner* — Brenda L Coleman
(74) *Attorney, Agent, or Firm* — Silvia Salvadori, P.C.; Silvia Salvadori

(57) ABSTRACT

Disclosed is a process for the purification of staurosporine (1), which comprises salification of staurosporine (1) (Formula (1)) by treatment with a mineral acid to give a precipitated salt, isolation of the staurosporine (1) precipitated salt, treatment of the staurosporine (1) isolated salt with an organic base, and isolation of staurosporine (1). Also disclosed are novel polymorphic forms of the mono- and bis-hydrochloride salts of staurosporine (1).

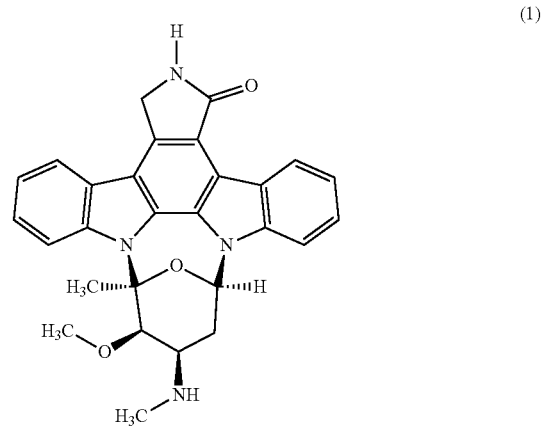

(1)

13 Claims, 1 Drawing Sheet

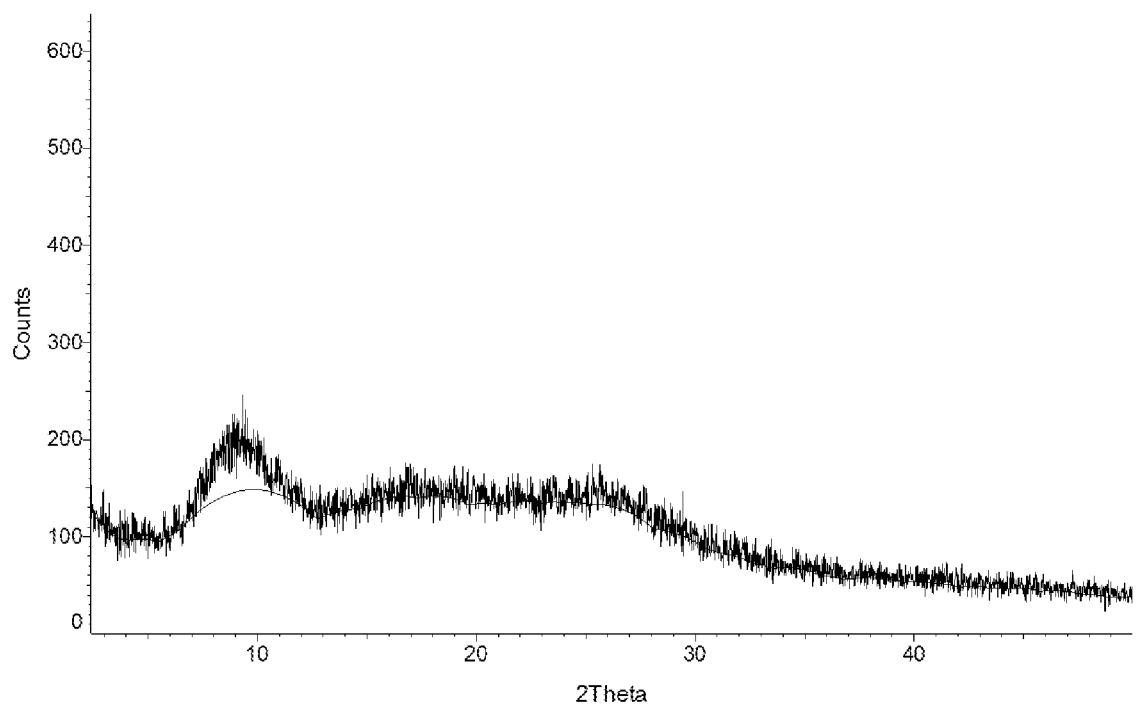

PROCESS FOR THE PURIFICATION OF INDOLE CARBAZOLE ALKALOIDS

This application is a U.S. national stage of PCT/IB2021/051683 filed on 1 Mar. 2021, which claims priority to and the benefit of Italian Patent Application No. 102020000004291 filed on 2 Mar. 2020, the contents of which are incorporated herein by reference in their entireties.

BACKGROUND TO THE INVENTION

Staurosporine (5S,6R,7R,9R)-6-methoxy-5-methyl-7-methylamino-6,7,8,9,15,16-hexahydroxy-5H,14H-5,9-epoxy-4b,9a,15-triazadibenzo[b,h]cyclonona[1,2,3,4-jkl]-cyclopenta[e]-as-indacen-14-one, having formula (1), is an indole carbazole alkaloid which can be isolated from the Gram-positive bacterium *Streptomyces staurosporeus*, as described by Ōmura et al. (J. Antibiot. 1977; 30 4:275-282).

Staurosporine (1)

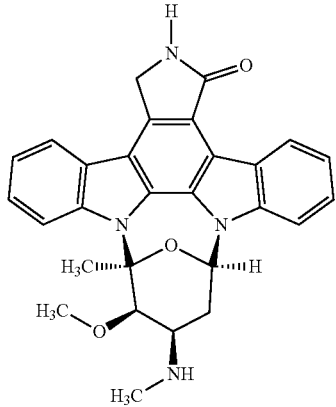

The compound, which is active as a protein kinase inhibitor, is used as intermediate in the preparation of midostaurin (N-[(5S,6R,7R,9R)-6-methoxy-5-methyl-14-oxo-6,7,8,9,15,16-hexahydro-5H,14H-5,9-epoxy-4b,9a,15-triazadibenzo[b,h]-cyclonona-[1,2,3,4-jkl]cyclopenta[e]-as-indacen-7-yl]-N-methylbenzamide) (2), an active ingredient indicated for the treatment of acute myeloid leukaemia, mast cell leukaemia, aggressive systemic mastocytosis, and systemic mastocytosis with associated haematological neoplasm.

Midostaurin (2)

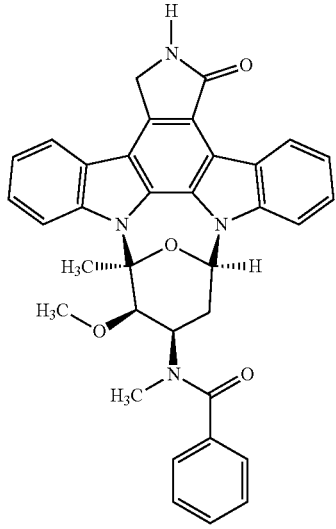

As staurosporine (1) is used to prepare active ingredient (2), it is essential to develop an isolation method which enables it to be obtained with the lowest possible impurity profile.

A classic isolation method involves purification of staurosporine with a chromatography process, as in Ōmura et al. (J. Antibiot. (1977); 30(4):275-282); however, said method is costly in terms of timing and materials when scaled up industrially. One solution to said problem is the use of an acid-base process which gives rise to the precipitation of a salt of staurosporine (1). For example, U.S. Pat. No. 8,710,216 discloses a process involving initial salification of staurosporine (1) with methanesulphonic acid, removal of impurities by treatment with activated carbon, separation of the solution containing the purified methanesulphonic salt, and reprecipitation of staurosporine (1) by treatment with a base. Using this procedure, a product with a purity level exceeding 98% can be obtained.

Patent CA1337763 relates to N-substituted derivatives of staurosporine (1), including midostaurin (2), and the preparation processes thereof; the various N-substituted derivatives of staurosporine (1) include the salts thereof, also cited as possible intermediates in purification processes. However, the Canadian patent does not indicate the purity level reached by said derivatives obtained from the corresponding salt, and neither describes nor quantifies the residual impurities. Moreover, in the experimental part, the purifications exemplified involve chromatographic purification or recrystallisation processes, but not acid-base processes.

Patent application US2005159404 refers to a possible use of staurosporine (1) salts or salts of derivatives thereof in purification or isolation processes, but once again, the problem of the content or nature of the impurities is not discussed.

In view of the use of staurosporine (1) as precursor of midostaurin (2), there is still a pressing need to develop other procedure for the isolation of staurosporine (1) with the lowest possible impurity levels.

DESCRIPTION OF THE INVENTION

The applicant has developed a process for the purification of staurosporine (1) which enables the percentage of impurities to be maintained at a lower value than that reported in the prior art. In fact, it has surprisingly been observed that treatment of an alcoholic solution of staurosporine (1) with a mineral acid, in particular with hydrochloric acid, not only causes precipitation of the corresponding salt (unlike the process reported in U.S. Pat. No. 8,710,216, wherein precipitation of methanesulphonic acid salt is not observed), but also affects the profile of the impurities present in staurosporine (1) free base. Even more surprisingly, the applicant has observed that different salts and different polymorphic forms are formed, depending on the amount of acid used to precipitate them.

A first aspect of the present invention is the process for the preparation of staurosporine (1) with a low impurity content, which involves initial treatment of crude staurosporine (1) with a mineral acid to give a precipitated salt, followed by isolation of the precipitated salt, then by treatment of the isolated salt with an organic base and finally, isolation of purified staurosporine (1) free base. For the purposes of the present invention, the term "crude staurosporine (1)" or "starting staurosporine (1)" means commercially available staurosporine (1) containing a mean percentage of total impurities by HPLC analysis ranging between 1% and 2%. HPLC purity is preferably determined by the method reported in the Methods section below.

A second aspect of the invention is represented by the staurosporine (1) salts obtained by treatment with a mineral acid, in particular with hydrochloric acid, and preferably with concentrated hydrochloric acid. Even more in particular, the salt obtained by treatment of staurosporine (1) with 37% concentrated hydrochloric acid is staurosporine (3) bis-hydrochloride salt. The amount of 37% hydrochloric acid added preferably ranges between 3 and 7 equivalents with respect to crude staurosporine (1).

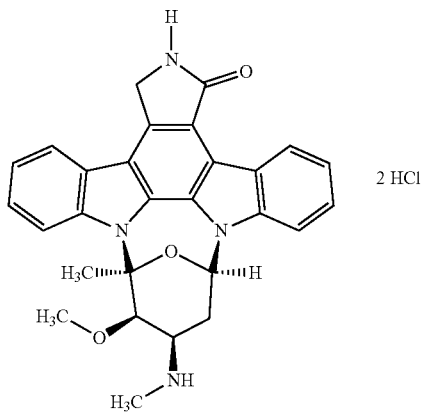

Staurosporine bis-hydrochloride (3)

A third aspect of the invention is represented by staurosporine (1) salts and the polymorphic forms of staurosporine bis-hydrochloride (3) salt. In particular, the polymorphic forms of staurosporine (3) bis-hydrochloride salt are Form A and Form B. The use of said polymorphic forms in the process according to the first aspect of the invention is surprisingly advantageous, as it enables the content of some impurities not eliminatable by similar methods reported in the prior art (such as the above-mentioned U.S. Pat. No. 8,710,216) to be reduced.

A fourth aspect of the invention is represented by the use of a mineral acid in liquid form, preferably 37% hydrochloric acid, to prepare the staurosporine (1) salts; in particular, said process has proved more advantageous than the one reported by Ōmura et al. as, especially on an industrial scale, the management of a liquid reagent is safer and more practical than that of a gaseous reagent. The amount of 37% hydrochloric acid added preferably ranges between 1 and 10 equivalents with respect to crude staurosporine (1). Even more particularly, the use of a mineral acid in liquid form, preferably 37% hydrochloric acid, gives rise not only to the staurosporine bis-hydrochloride salt (3), but also to a staurosporine mono-hydrochloride salt (4) in crystalline form, not in amorphous form, as in the process reported by Ōmura et al.

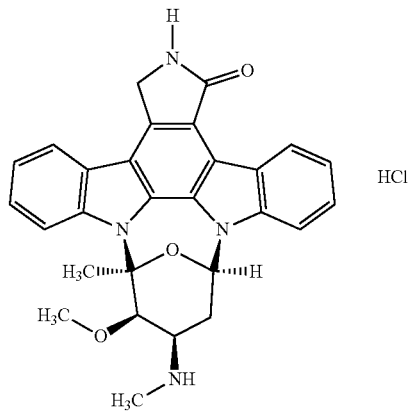

Staurosporine mono-hydrochloride (4)

With special reference to the first aspect of the invention, a preferred embodiment is represented by process 1, which involves the following steps:
a. adding a polar protic solvent to staurosporine (1), thereby forming reaction mixture A;
b. heating reaction mixture A;
c. adding a mineral acid to reaction mixture A, thereby forming reaction mixture B;
d. cooling reaction mixture B;
e. isolating the staurosporine salt from reaction mixture B;
f. adding a polar protic solvent to the staurosporine salt, thereby forming reaction mixture C;
g. heating reaction mixture C;
h. adding a base to reaction mixture C, thereby forming reaction mixture D;
i. cooling reaction mixture D;
j. isolating staurosporine (1) from reaction mixture D.

In a preferred aspect, the polar protic solvent used in step a is a straight or branched $C_1$-$C_4$ aliphatic alcohol, preferably methanol.

In a further preferred aspect, in step b, reaction mixture A is heated to a temperature ranging between 40° C. and 120° C.; the heating temperature is preferably 65° C. (reflux temperature of methanol).

In a further preferred aspect, the mineral acid used in step c is selected from hydrofluoric acid, hydrobromic acid, hydrochloric acid, perchloric acid, hydroiodic acid, nitric acid, phosphoric acid, sulphuric acid and boric acid; preferably 37% hydrochloric acid.

In a further preferred aspect of the embodiment, the amount of 37% hydrochloric acid added to reaction mixture A ranges between 1 equivalent and 10 equivalents with respect to staurosporine (1).

In a further preferred aspect, the amount of 37% hydrochloric acid ranges between 1 and 1.5 equivalents with respect to staurosporine (1).

In a further preferred aspect, the amount of 37% hydrochloric acid ranges between 3 and 3.5 equivalents with respect to staurosporine (1).

In a further preferred aspect, the amount of 37% hydrochloric acid ranges between 6 and 7 equivalents with respect to staurosporine (1).

In a further preferred aspect, reaction mixture B is cooled to a temperature ranging between −10° C. and 40° C., preferably to 20° C.

Typically, in step e, the staurosporine salt is isolated using one of the conventional solid-liquid separation techniques such as filtration, centrifugation, distillation and decanting; the staurosporine salt is preferably isolated by filtration.

In a further aspect, the polar protic solvent used in step f is a straight or branched $C_1$-$C_4$ aliphatic alcohol, preferably methanol.

In a further preferred aspect, in step g, reaction mixture C is heated to a temperature ranging between 40° C. and 120° C.; the heating temperature is preferably 65° C. (reflux temperature of methanol).

In a further preferred aspect, the base used in step h is selected from ammonia and primary, secondary or tertiary aliphatic or aromatic amines; more preferably, the base used is triethylamine.

In a further aspect, the amount of triethylamine added to reaction mixture C ranges between 1 equivalent and 10 equivalents, and the triethylamine preferably ranges between 1 and 4 equivalents with respect to the starting staurosporine (1).

In a further preferred aspect, in step i, reaction mixture D is cooled to a temperature ranging between −10° C. and 40° C.; more preferably the suspension is cooled to 25° C.

In a further preferred aspect, in step J, purified staurosporine (1) is isolated using one of the conventional solid-liquid separation techniques such as filtration, centrifugation, distillation and decanting; the purified staurosporine (1) is preferably isolated by filtration.

Typically, purified staurosporine (1) is isolated with a impurity content between 50% and 100% lower, and more preferably between 60% and 100%, lower than that of the starting staurosporine (1).

With particular reference to the polymorphic forms of staurosporine bis-hydrochloride salt (3), which are the third aspect of the present invention, a preferred embodiment is represented by polymorphic solid Form A, the XRPD spectrum of which exhibits a crystalline structure and comprises distinctive reflections, expressed as 2θ° angles, with a relative intensity greater than or equal to 5%, approximately amounting to: 6.8-9.1-13.5-27.0-27.7-33.9 (±0.2). In detail, the XRPD spectrum of Form A exhibits a crystalline structure and comprises distinctive reflections, expressed as 2θ° angles, with a relative intensity greater than 1%, approximately amounting to: 6.2-6.8-7.0-9.1-13.5-14.1-14.8-16.8-18.2-20.2-21.1-21.8-23.6-24.3-26.8-27.0-27.7-28.3-32.9-33.9-42.8-48.1 (±0.2). In even more detail, the XRPD spectrum of Form A exhibits a crystalline structure and comprises distinctive reflections, expressed as 2θ° angles, approximately amounting to: 6.2-6.8-7.0-9.1-11.8-12.2-13.5-14.1-14.3-14.8-15.7-16.0-16.8-18.2-19.0-19.7-20.2-20.6-21.1-21.5-21.8-22.3-23.6-24.3-24.9-26.0-26.8-27.0-27.7-28.3-28.7-29.3-29.7-30.6-31.1-31.5-32.0-32.9-33.9-35.5-38.8-40.9-41.5-42.8-48.1 (±0.2).

A further preferred aspect is represented by the process for the purification of staurosporine (1) which involves isolating staurosporine bis-hydrochloride (3) Form A in step e; said process, which comprises steps a-j as in process 1, preferably involves the use in step c of an amount of 37% hydrochloric acid ranging between 6 and 7 equivalents, preferably 6.7 equivalents, with respect to staurosporine (1).

In a further preferred aspect, the amount of triethylamine added to reaction mixture C in step h is 2.1 equivalents with respect to the starting staurosporine (1).

In a further preferred aspect, staurosporine (1) is isolated with an impurity content 50-100% lower than that of the starting staurosporine (1); in an even more advantageous aspect, the impurity content is preferably at least 65% lower.

In a further preferred aspect, the amount of the impurities with retention time 0.668 (hereinafter called "Impurities 5 and 6") is 50-100% lower than that of crude staurosporine (1), depending on the HPLC method used (described in the Methods section); preferably, in an even more advantageous aspect, the impurity content with retention time 0.668 is at least 79% lower, depending on the HPLC method used.

Again with reference to the polymorphic forms of staurosporine bis-hydrochloride (3) salt, a further preferred embodiment is represented by solid polymorphic Form B, the XRPD spectrum of which exhibits a crystalline structure and comprises distinctive reflections, expressed as 2θ° angles, with a relative intensity greater than 5%, approximately amounting to: 6.2-9.2-9.8-11.3-12.4-20.1-21.8-25.8 (±0.2). In detail, the XRPD spectrum of Form B exhibits a crystalline structure and comprises distinctive reflections, expressed as 2θ° angles, with a relative intensity greater than 1%, approximately amounting to: 6.2-8.4-9.2-9.8-10.3-11.3-12.4-12.8-14.6-15.0-17.2-17.8-18.4-18.9-19.7-20.1-20.6-21.8-22.3-23.1-24.4-25.0-25.8-26.1-27.0-30.2-32.1-40.9 (±0.2). In even more detail, the XRPD spectrum of Form B exhibits a crystalline structure and comprises distinctive reflections, expressed as 2θ° angles, approximately amounting to 5.7-6.2-7.6-8.4-9.2-9.8-10.3-11.3-12.4-12.8-13.8-14.6-15.0-15.8-17.2-17.8-18.4-18.9-19.2-19.7-20.1-20.6-21.8-22.3-22.8-23.1-23.9-24.4-25.0-25.8-26.1-27.0-28.2-28.9-30.2-32.1-33.0-34.9-35.9-37.5-38.6-40.9 (±0.2).

A further preferred aspect is represented by the process for the purification of staurosporine (1), which involves isolating staurosporine bis-hydrochloride (3) Form B; said process, which comprises steps a-j as in process 1, preferably involves the use in step c of an amount of 37% hydrochloric acid ranging between 3 and 3.5 equivalents, preferably 3.1 equivalents, with respect to staurosporine (1).

In a further preferred aspect, the amount of triethylamine added to reaction mixture C in step h is 3.6 equivalents with respect to the starting staurosporine (1).

In a further preferred aspect, heating of reaction mixture C in step g is optional.

In a further preferred aspect of the invention, the purified staurosporine (1) is isolated with an impurity content 50-100% lower than that of the starting staurosporine (1); the impurity content is preferably at least 74% lower.

With special reference to the fourth aspect of the invention, an advantageous embodiment is represented by the solid form of staurosporine mono-hydrochloride (4) salt, the XRPD spectrum of which exhibits a crystalline structure and comprises distinctive reflections, expressed as 2θ° angles, with a relative intensity greater than 5%, approximately amounting to: 4.9-9.8-14.6-19.5 (±0.2). In detail, the XRPD spectrum of the salt of staurosporine mono-hydrochloride (4) exhibits a crystalline structure and comprises distinctive reflections, expressed as 2θ° angles, with a relative intensity greater than 1%, approximately amounting to: 4.9-5.7-8.0-8.7-9.8-14.6-15.3-16.8-17.6-19.5-23.6-24.4-26.5-34.4 (±0.2). In even more detail, the XRPD spectrum of the salt of staurosporine mono-hydrochloride (4) exhibits a crystalline structure and comprises distinctive reflections, expressed as 2θ° angles, approximately amounting to: 4.9-6.8-5.7-8.0-8.7-9.8-12.5-14.6-15.3-16.8-17.6-19.5-23.6-24.4-25.0-26.5-29.3-34.4-39.9-44.7 (±0.2).

A further preferred aspect of the embodiment is represented by process 2 for the preparation of staurosporine mono-hydrochloride (4); said process, which comprises steps a-e as in process 1, preferably involves the use in step c of an amount of 37% hydrochloric acid ranging between 1 and 1.5 equivalents, preferably 1.1 equivalents, of staurosporine (1).

EXPERIMENTAL SECTION

The diffraction grid was recorded with a Bruker D2-Phaser with the following parameters:
Anode tube: Cu
Voltage generator (kV): 30
Current generator (mA): 10
Wavelength $\lambda_1$ and $\lambda_2$ (Å): 1.54056, 1.54439
Intensity ratio ($\lambda_2/\lambda_1$): 0.500
Spinner: off
Angle range (2θ°): 2.00-50.00
Step size (2θ°): 0.020
Time per step (sec): 3.0

The analyses of the impurity content of staurosporine (1), the staurosporine mono-hydrochloride salt (4) and staurosporine bis-hydrochloride (3) were conducted by HPLC, using the instrumentation and conditions reported below.

HPLC system comprising a quaternary pump, a compartment with thermostated column and UV/Vis detector, connected to Empower software or equivalent.

Column
Stationary phase: Gemini NX C 18.
Dimensions: l=150 mm; I.D.=4.6 mm, particle size 3 μm.
Manufacturer: Phenomenex; P/N: 00F-4453-E0.

Mobile phase
Solvent A: 5 mM ammonium bicarbonate in water (pH adjusted to 10.0) and addition of 0.1 mM EDTA
Solvent B: Acetonitrile

| Linear gradient | | |
| --- | --- | --- |
| Time (min) | Solvent A (%) | Solvent B (%) |
| 0.0 | 55 | 45 |
| 9.0 | 30 | 70 |
| 11.0 | 5 | 95 |
| 14.0 | 5 | 95 |
| 14.5 | 55 | 45 |
| 20 | 55 | 45 |

Analysis conditions
Flow rate: 0.8 ml/minute
Detection: 294 nm
Injection volume: 10 μl
Column temperature: 30° C.
Autosampler temperature: 5° C.
Run time: 20 minutes

PREPARATION EXAMPLES

Example 1 (According to the Invention)—Purification of Staurosporine (1)

Preparation of Staurosporine Bis-Hydrochloride (3) Form a (Steps a-e)

Staurosporine (1) (4.58 Kg, HPLC assay value 88%, 8.66 mol) was added to methanol (22.5 L); a 37% solution of hydrochloric acid (6.7 eq., 4.87 L, 58 mol) in methanol (18 L) was dropped into the resulting reaction mixture, heated to reflux. Complete dissolution of the solid was observed at the end of the additions. The resulting reaction mixture was maintained under stirring and under reflux for two hours, during which time a second mustard-yellow solid precipitated. The suspension was cooled to room temperature, and 5.5 Kg of staurosporine bis-hydrochloride (4) Form A was obtained after filtration.

| Retention time | Identification | Molecular weight | Crude staurosporine (1) | Staurosporine bis-hydrochloride (3) Form A |
| --- | --- | --- | --- | --- |
| 0.423 | Impurity 1 | 628 | 0.10 | 0.02 |
| 0.589 | Impurity 2 | 482 | 0.08 | 0.04 |
| 0.605 | Impurities 3 and 4 | 311 and 482 | 0.03 | — |
| 0.668 | Impurities 5 and 6 | 482 and 452 | 0.24 | 0.06 |
| 0.682 | Impurity 14 | — | 0.08 | — |
| 0.728 | Impurity 7 | 452 | 0.02 | 0.02 |
| 0.739 | Impurity 8 | 482 | 0.07 | — |
| 0.8 | Impurity 9 | 482 | 0.02 | — |
| 0.91 | Impurity 15 | — | 0.04 | — |
| 0.965 | Impurity 11 | 480 | 0.18 | 0.15 |
| 1 | Staurosporine | 466 | 98.55 | 99.60* |
| 1.088 | Impurity 12 | 496 | 0.47 | — |
| 1.11 | Impurity 13 | 496 | 0.07 | 0.02 |
| 1.402 | Impurity 27 | — | — | 0.03 |
| 1.601 | Impurity 26 | — | — | 0.03 |

*Under the effect of the eluent mixture, staurosporine bis-hydrochloride (3) Form A dissociates to give staurosporine (1).

The percentage of total impurities, measured by the HPLC method reported above, fell from 1.45% to 0.4%.

The XRPD spectrum of Form A exhibits a crystalline structure and comprises distinctive reflections, expressed as 2θ° angles, approximately amounting to:
1) 6.8-9.1-13.5-27.0-33.9 (±0.2), relative intensity greater than or equal to 5%;
2) 6.2-7.0-14.1-14.8-16.8-18.2-20.2-21.1-21.8-23.6-24.3-26.8-27.7-28.3-32.9-42.8-48.1 (±0.2), relative intensity between 1% and 5% extremes excluded, i.e. greater than 1% and less than 5%;
3) 11.8-12.2-14.3-15.7-16.0-19.0-19.7-20.6-21.5-22.3-24.9-26.0-28.7-29.3-29.7-30.6-31.1-31.5-32.0-35.5-38.8-40.9-41.5 (±0.2), relative intensity less than or equal to 1%.

Preparation of Staurosporine (1) Free Base (Steps f-j)

Staurosporine bis-hydrochloride (4) Form A, obtained in step e was added to methanol (15 L); triethylamine (2.5 L, 2.1 eq., 18.2 mol) (pH>8.5) was added to the reaction mixture, which was then heated to reflux and maintained under stirring for one hour. The reaction mixture was cooled to room temperature and filtered. The resulting solid was washed with methanol (2×5 L) and then dried at 60° C. under vacuum for 20 hours. 3.74 Kg of staurosporine (1) free base was obtained.

| Retention time | Identification | Molecular weight | Pure staurosporine (1) |
| --- | --- | --- | --- |
| 0.589 | Impurity 2 | 482 | 0.02 |
| 0.668 | Impurities 5 and 6 | 482 + 452 | 0.05 |
| 0.728 | Impurity 7 | 452 | 0.02 |
| 0.843 | Impurity 28 | | 0.03 |
| 0.965 | Impurity 11 | 480 | 0.12 |
| 1 | Staurosporine (1) | 466 | 99.76 |

The percentage of total impurities, measured by the HPLC method reported above, fell from 0.4% to 0.14%. Considering the entire process 1 (steps a-j), a total reduction of impurities amounting to 65% is observed.

It is noteworthy that the percentage of impurities 5 and 6, recorded at retention time 0.668 by applying the HPLC method reported above, falls from 0.24% to 0.05%. This result, which corresponds to a 79.1% reduction in the amount of impurities 5 and 6, is surprising, because when similar methods reported in the prior art (such as the above-mentioned U.S. Pat. No. 8,710,216) are used, the percentage of said impurities remains unchanged, as demonstrated by Example 4 (comparative) below.

The XRPD spectrum of staurosporine (1) exhibits a crystalline structure and comprises distinctive reflections, expressed as 2θ° angles, approximately amounting to:
1) 8.0-8.5-12.4-12.8-13.0-14.7-16.3-16.9-18.1-19.1-23.2-24.2 (±0.2), relative intensity greater than or equal to 5%;
2) 6.4-7.7-11.6-17.6-20.2-21.0-22.5-24.7-25.5-26.1-26.6-28.9-29.6-29.8-30.4-31.6-32.4-36.5-42.8-45.4 (±0.2), relative intensity between 1% and 5% extremes excluded, ie. greater than 1% and less than 5%;
3) 27.4-27.9-34.7-37.1-37.5-38.5-38.9-40.4-46.5 (±0.2), relative intensity less than or equal to 1%.

Example 2 (According to the Invention)—Purification of Staurosporine (1)

Preparation of Staurosporine Bis-Hydrochloride (3) Form B (Steps a-e))

Staurosporine (1) (1 g, HPLC assay value 88%, 1.89 mmol) was suspended in methanol (5 mL); a 37% solution of hydrochloric acid (3.1 eq., 0.49 mL, 5.9 mmol) in methanol (1 mL) was dropped into the reaction mixture, heated to reflux. Complete dissolution of the solid was observed at the end of the additions. The resulting mixture was maintained under stirring at reflux for 15 minutes, during which time a yellow crystalline solid precipitated. The mixture was cooled to room temperature, and 928 mg of staurosporine bis-hydrochloride (3) Form B was obtained after filtration.

The percentage of total impurities, measured by the HPLC method reported above, fell from 1.3% to 0.5%.

| Retention time | Identification | Molecular weight | Crude staurosporine (1) | Staurosporine bis-hydrochloride (3) Form A | Pure staurosporine (1) |
|---|---|---|---|---|---|
| 0.423 | Impurity 1 | 628 | 0.06 | — | — |
| 0.605 | Impurities 3 and 4 | 311 + 482 | 0.03 | 0.02 | — |
| 0.668 | Impurities 5 and 6 | 482 + 452 | 0.14 | 0.02 | — |
| 0.682 | Impurity 14 | | 0.13 | 0.07 | 0.07 |
| 0.728 | Impurity 7 | 452 | 0.02 | 0.02 | 0.02 |
| 0.739 | Impurity 8 | 482 | 0.02 | — | — |
| 0.8 | Impurity 9 | 482 | 0.02 | — | — |
| 0.838 | Impurity 10 | 451 | 0.09 | 0.03 | 0.03 |
| 0.91 | Impurity 15 | | 0.04 | — | — |
| 0.965 | Impurity 11 | 480 | 0.2 | 0.18 | 0.14 |
| 1 | Staurosporine (1) | 466 | 98.61 | 99.47* | 99.64 |
| 1.088 | Impurity 12 | 496 | 0.39 | 0.11 | 0.08 |
| 1.11 | Impurity 13 | 496 | 0.18 | 0.05 | — |

*Under the effect of the eluent mixture, staurosporine bis-hydrochloride (3) Form B dissociates to give staurosporine (1).

The XRPD spectrum of Form B exhibits a crystalline structure and comprises distinctive reflections, expressed as 2θ° angles, approximately amounting to:
1) 6.2-9.2-9.8-11.3-12.4-20.1-21.8-25.8 (±0.2), relative intensity greater than or equal to 5%;
2) 8.4-10.3-12.8-14.6-15.0-17.2-17.8-18.4-18.9-19.7-20.6-22.3-23.1-24.4-25.0-26.1-27.0-30.2-32.1-40.9 (±0.2), relative intensity ranging between 1% and 5% extremes excluded, ie. greater than 1% and less than 5%;
3) 5.7-7.6-13.8-15.8-19.2-22.8-23.9-28.2-28.9-33.0-34.9-35.9-37.5-38.6 (±0.2), relative intensity less than or equal to 1%.

Preparation of Staurosporine (1) Free Base (Steps f-j)

Staurosporine bis-hydrochloride (3) Form B, obtained in step e was added to methanol; triethylamine (693 mg, 3.6 eq, 6.86 mmol) was added to the reaction mixture. The mixture was stirred for 15 minutes and then filtered. The resulting solid was washed with methanol (1.5 mL) and then dried at 60° C. under vacuum for 20 hours. 928 mg of staurosporine (1) free base was obtained.

The percentage of total impurities, measured by the HPLC method reported above, fell from 0.5% to 0.34%. Considering the entire process 1 (steps j), a total reduction of impurities amounting to 74% is observed.

Example 3 (According to the Invention)—Purification of Staurosporine (1)

Preparation of Staurosporine Mono-Hydrochloride (4) (Steps a-e)

Staurosporine (1) (5 g, HPLC titre 88%, 9.44 mmol) was added to methanol (20 mL); a solution of 37% hydrochloric acid (1.03 g, 1.1 eq., 10.38 mmol) was added drop by drop to the reaction mixture, heated to reflux. After 30 minutes at reflux and under stirring, the suspension was cooled to room temperature and filtered.

The percentage of impurities, measured by the HPLC method reported above, is 0.59%.

The XRPD spectrum of staurosporine mono-hydrochloride (4) exhibits a crystalline structure and comprises distinctive reflections, expressed as 2θ° angles, approximately amounting to:
1) 4.9-9.8-14.6-19.5 (±0.2), relative intensity greater than or equal to 5%;
2) 5.7-8.0-8.7-15.3-16.8-17.6-23.6-24.4-26.5-34.4 (±0.2), relative intensity ranging between 1% and 5% extremes excluded, ie. greater than 1% and less than 5%;
3) 6.8-12.5-25.0-29.3-39.9-44.7 (±0.2), relative intensity less than or equal to 1%.

Preparation of Staurosporine (1) Free Base (Steps f-j)

Staurosporine mono-hydrochloride (4) obtained in step e was added to methanol (17.5 mL); triethylamine (1.15 g, 1.2 eq., 11.4 mmol) (pH>8.5) was added to the mixture, and the mixture was then heated to reflux and maintained under stirring for one hour. The reaction mixture was cooled to room temperature and filtered. The resulting solid was washed with methanol (2×10 mL) and then dried at 60° C. under vacuum for 20 hours. 3.7 g of staurosporine (1) was obtained.

Example 4 (Comparative)—Purification of Staurosporine (1), According to U.S. Pat. No. 8,710,216

Staurosporine (1) (5 g, HPLC titre 88%, 9.44 mmol) was suspended in ethanol (22 mL); methanesulphonic acid (1 g, 10.37 mmol, 1.1 eq.) was added to the reaction mixture, heated to 70° C. Complete dissolution of the solid was observed. The reaction mixture obtained after addition of activated carbon (0.44 g) and celite (2 g) was maintained at 70° C. for one hour. The reaction mixture was then filtered hot, and the solid residue washed with ethanol (2×4.5 mL). Triethylamine (1.15 g, 11.31 mmol, 1.2 eq.) in ethanol (4.5 mL) was added drop by drop to the filtrate, cooled to 60° C. The mixture obtained as a result of the additions was maintained under stirring at 60° C. for 30 minutes, then cooled to 20° C. and maintained under stirring for a further 16 hours. After filtration of the suspension and washing of the solid residue with ethanol (2×4.5 mL), 5.88 g of wet solid was obtained; by stove-drying at 60° C. under vacuum for 20 h, 4.25 g of staurosporine (1) was obtained

| Retention time | Identification | Molecular weight | Crude staurosporine (1) | Pure staurosporine (1) |
|---|---|---|---|---|
| 0.423 | Impurity 1 | 628 | 0.06 | — |
| 0.589 | Impurity 2 | 482 | 0.02 | 0.02 |
| 0.605 | Impurities 3 and 4 | 311 + 482 | 0.03 | — |
| 0.668 | Impurities 5 and 6 | 482 + 452 | 0.14 | 0.14 |
| 0.682 | Impurity 14 | | 0.13 | 0.12 |
| 0.728 | Impurity 7 | 452 | 0.02 | — |
| 0.739 | Impurity 8 | 482 | 0.02 | — |
| 0.800 | Impurity 9 | 482 | 0.02 | — |
| 0.838 | Impurity 10 | 451 | 0.09 | 0.07 |
| 0.910 | Impurity 15 | | 0.04 | 0.04 |
| 0.965 | Impurity 11 | 480 | 0.2 | 0.17 |
| 1.000 | Staurosporine (1) | 466 | 98.61 | 98.63 |
| 1.088 | Impurity 12 | 496 | 0.39 | — |
| 1.110 | Impurity 13 | 496 | 0.18 | — |
| 1.215 | Impurity 16 | | — | 0.17 |
| 1.251 | Impurity 17 | | — | 0.03 |
| 1.509 | Impurity 18 | | — | 0.02 |
| 1.529 | Impurity 19 | | — | 0.03 |
| 1.622 | Impurity 20 | | — | 0.08 |
| 1.727 | Impurity 21 | | — | 0.48 |
| 1.777 | Impurity 22 | | — | 0.03 |

Example 5 (Comparative)—Purification of Staurosporine (1), as Described in Ōmura et al. (J. Antibiot. (1977); 30(4):275-282)

Staurosporine (5 g, HPLC assay value 88%, 9.44 mol) was dissolved in 250 mL of CHCl$_3$, and gaseous HCl (generated separately by dropping 37% HCl into 98% H$_2$SO$_4$) was then bubbled into the reaction mixture.

A white crystallised solid formed during bubbling. Bubbling was interrupted when no further crystallisate appeared (a total of 2.8 g of 37% HCl, about 3 eq., was dropped in). The solid was filtered and stove-dried at 50° C. for 18 h. 4.4 g of staurosporine mono-hydrochloride (4) was obtained.

| Retention time | Identification | Molecular weight | Crude staurosporine (1) | Staurosporine mono-hydro chloride (4) |
|---|---|---|---|---|
| 0.423 | Impurity 1 | 628 | 0.06 | 0.05 |
| 0.463 | Impurity 27 | | 0.02 | — |
| 0.565 | Impurity 28 | | — | 0.02 |
| 0.589 | Impurity 2 | 482 | 0.06 | 0.08 |
| 0.647 | Impurity 29 | | 0.02 | — |
| 0.668 | Impurities 5 and 6 | 482 + 452 | 0.29 | 0.28 |
| 0.711 | Impurity 30 | | 0.02 | 0.03 |
| 0.739 | Impurity 8 | 482 | 0.02 | — |
| 0.8 | Impurity 9 | 482 | 0.04 | — |
| 0.807 | Impurity 31 | | 0.02 | — |
| 0.838 | Impurity 10 | 451 | 0.12 | 0.07 |
| 0.91 | Impurity 15 | | 0.04 | 0.04 |
| 0.965 | Impurity 11 | 480 | 0.21 | 0.19 |
| 1 | Staurosporine (1) | 466 | 98.58 | 98.55* |
| 1.088 | Impurity 12 | 496 | 0.37 | 0.42 |
| 1.11 | Impurity 13 | 496 | 0.15 | 0.16 |
| 1.161 | Impurity 32 | | — | 0.02 |
| 1.239 | Impurity 33 | | — | 0.02 |
| 1.283 | Impurity 34 | | — | 0.04 |
| 1.781 | Impurity 35 | | — | 0.02 |

*Under the effect of the eluent mixture, staurosporine mono-hydrochloride (4) dissociates to give staurosporine (1).

The XRPD of the hydrochloride salt (amorphous) is shown in The FIGURE.

The invention claimed is:

1. A process for the purification of staurosporine (1),

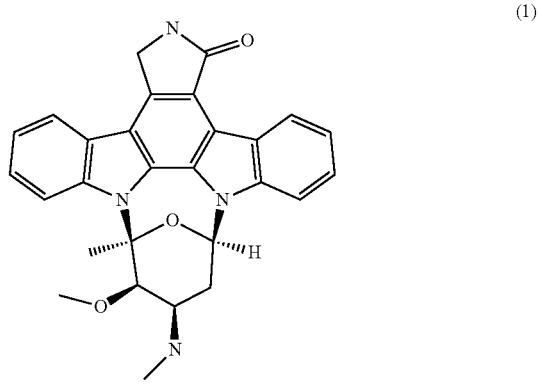 [SMILES: CN[C@@H]1C[C@H]2O[C@@](C)([C@@H]1OC)n1c3ccccc3c3c4c(c5c6ccccc6n2c5c31)C(=O)NC4]

(1)

which comprises salification of staurosporine (1) by treatment with a mineral acid to give a precipitated salt, isolation of the precipitated salt of staurosporine (1), treatment of the isolated salt of staurosporine (1) with an organic base selected from ammonia, primary, secondary, tertiary aliphatic amine or primary, secondary, tertiary aromatic amine, and isolation of staurosporine (1).

2. The process according to claim 1, which comprises the following steps:
   step a adding a polar protic solvent to staurosporine (1), wherein said polar protic solvent is selected from straight or branched C$_1$-C$_4$ aliphatic alcohol, thereby forming reaction mixture A;
   step b heating reaction mixture A to a temperature ranging from 40° C. to 120° C.;
   step c adding a mineral acid to reaction mixture A, thereby forming reaction mixture B;
   step d cooling reaction mixture B to a temperature ranging from −10° C. to 40° C.;
   step e isolating the staurosporine salt from reaction mixture B;
   step f adding a polar protic solvent to the staurosporine salt, wherein said polar protic is a straight or branched C$_1$-C$_4$ aliphatic alcohol, thereby forming reaction mixture C;

step g heating reaction mixture C to a temperature ranging from 40° C. to 120° C.;
step h adding an organic base to reaction mixture C, wherein said organic base is selected from ammonia, primary, secondary or tertiary aliphatic or aromatic amines, thereby forming reaction mixture D;
step i cooling reaction mixture D to a temperature ranging from −10° C. to 40° C.; and
step j isolating staurosporine (1) from reaction mixture D.

3. The process according to claim 2, wherein in step c the mineral acid is selected from hydrofluoric acid, hydrobromic acid, hydrochloric acid, perchloric acid, hydroiodic acid, nitric acid, phosphoric acid, sulphuric acid and boric acid.

4. The process according to claim 3, comprising the use of 37% hydrochloric acid in step c.

5. The process according to claim 4, comprising the use of 37% hydrochloric acid in the amount of between 1 and 10 equivalents with respect to staurosporine (1) in step c.

6. The process according to claim 4, comprising the use of 37% hydrochloric acid in the amount of 1.1 equivalents with respect to staurosporine (1) in step c.

7. The process according to claim 4, comprising the use of 37% hydrochloric acid in the amount of 3.1 equivalents with respect to of staurosporine (1) in step c.

8. The process according to claim 4, comprising the use of 37% hydrochloric acid in the amount of 6.7 equivalents of staurosporine (1) in step c.

9. The staurosporine bis-hydrochloride salt (3)

(3)

2 HCl in its polymorphic form, Form A, with a crystalline structure and XRPD spectrum comprising distinctive reflections, expressed as 2θ° angles, approximately equal to:
I  6.8-9.1-13.5-27.0-33.9 (±0.2), relative intensity greater than or equal to 5%;
II  6.2-7.0-14.1-14.8-16.8-18.2-20.2-21.1-21.8-23.6-24.3-26.8-27.7-28.3-32.9-42.8-48.1 (±0.2), relative intensity between 1% and 5% extremes excluded;
III  11.8-12.2-14.3-15.7-16.0-19.0-19.7-20.6-21.5-22.3-24.9-26.0-28.7-29.3-29.7-30.6-31.1-31.5-32.0-35.5-38.8-40.9-41.5 (±0.2), relative intensity less than or equal to 1%.

10. The staurosporine bis-hydrochloride salt (3) in its polymorphic form Form B, with a crystalline structure and XRPD spectrum comprising distinctive reflections, expressed as 2θ° angles, approximately equal to:
I  6.2-9.2-9.8-11.3-12.4-20.1-21.8-25.8 (±0.2), relative intensity greater than or equal to 5%;
II  8.4-10.3-12.8-14.6-15.0-17.2-17.8-18.4-18.9-19.7-20.6-22.3-23.1-24.4-25.0-26.1-27.0-30.2-32.1-40.9 (±0.2), relative intensity between 1% and 5%, extremes excluded;
III  5.7-7.6-13.8-15.8-19.2-22.8-23.9-28.2-28.9-33.0-34.9-35.9-37.5-38.6 (±0.2), relative intensity less than or equal to 1%.

11. The staurosporine monohydrochloride salt (4)

(4)

HCl with a crystalline structure and XRPD spectrum comprising distinctive reflections, expressed as 2θ° angles, approximately equal to:
I 4.9-9.8-14.6-19.5 (±0.2), relative intensity greater than or equal to 5%;
II 5.7-8.0-8.7-15.3-16.8-17.6-23.6-24.4-26.5-34.4 (±0.2), relative intensity between 1% and 5% extremes excluded;
III 6.8-12.5-25.0-29.3-39.9-44.7 (±0.2), relative intensity less than or equal to 1%.

12. The process according to claim 1, wherein said organic base is triethylamine.

13. The process according to claim 2, wherein said polar protic solvent is methanol.

* * * * *